(12) United States Patent  
Chevallier

(10) Patent No.: US 9,314,575 B2  
(45) Date of Patent: Apr. 19, 2016

(54) PROTECTED INJECTION SYRINGE DEVICE

(75) Inventor: Stéphane Chevallier, Saint-Pathus (FR)

(73) Assignee: Tech Group Europe Limited, Dublin (IE)

( * ) Notice: Subject to any disclaimer, the term of this patent is extended or adjusted under 35 U.S.C. 154(b) by 870 days.

(21) Appl. No.: 10/576,938

(22) PCT Filed: Oct. 18, 2004

(86) PCT No.: PCT/FR2004/002654
§ 371 (c)(1),
(2), (4) Date: Aug. 23, 2006

(87) PCT Pub. No.: WO2005/039678
PCT Pub. Date: May 6, 2005

(65) Prior Publication Data
US 2007/0179441 A1    Aug. 2, 2007

(30) Foreign Application Priority Data
Oct. 22, 2003    (FR) ...................................... 03 12327

(51) Int. Cl.
*A61M 5/32*    (2006.01)
*A61M 5/31*    (2006.01)
*A61M 5/315*    (2006.01)

(52) U.S. Cl.
CPC .............. *A61M 5/326* (2013.01); *A61M 5/3257* (2013.01); *A61M 5/3135* (2013.01);
(Continued)

(58) Field of Classification Search
CPC ..................... A61M 5/326; A61M 2005/3247; A61M 5/3257; A61M 5/3243; A61M 2005/3261; A61M 5/3271; A61M 2005/31508; A61M 25/0631; A61M 5/3135; A61M 5/31501; A61M 5/3245; A61M 2005/3264; A61M 5/3275; A61M 5/31566; A61M 2005/3246; A61M 2005/3252; A61M 2005/3265; A61M 2005/3268
USPC .................................. 604/110, 192, 197, 198
See application file for complete search history.

(56) References Cited

U.S. PATENT DOCUMENTS 1,921,034 A    8/1933  La Marche
3,880,163 A    4/1975  Ritterskamp
(Continued)

FOREIGN PATENT DOCUMENTS

EP    0904792 A2    3/1999
EP    0966983 A1    12/1999
(Continued)

OTHER PUBLICATIONS

Office Action issued Oct. 24, 2013 in U.S. Appl. No. 11/861,567 by Pessin.

(Continued)

*Primary Examiner* — Bhisma Mehta
*Assistant Examiner* — Laura Schell
(74) *Attorney, Agent, or Firm* — Panitch Schwarze Belisario & Nadel LLP

(57) ABSTRACT

The device comprises a syringe (10, 11, 12) and safety means comprising a protective sheath (16) capable of adopting, relative to the syringe body, both an injection configuration in which the syringe needle (11) projects beyond said sheath, and a protection configuration in which the needle extends inside the sheath. The device includes a trigger member (30) enabling it to pass from the injection configuration to the protection configuration at the end of the injection stroke. It comprises means (34) for defining a first end-of-injection-stroke situation in which the trigger member (30) is unsuitable for causing the device to pass from the injection configuration to the protection configuration, and a second end-of-injection-stroke situation in which such passage is possible.

11 Claims, 4 Drawing Sheets

(52) U.S. Cl.
CPC ......... *A61M 5/31501* (2013.01); *A61M 5/3202* (2013.01); *A61M 5/3243* (2013.01); *A61M 2005/31508* (2013.01); *A61M 2005/3247* (2013.01); *A61M 2005/3261* (2013.01); *A61M 2005/3264* (2013.01)

(56) References Cited

U.S. PATENT DOCUMENTS

| | | |
|---|---|---|
| 4,631,057 A | 12/1986 | Mitchell |
| 4,723,943 A | 2/1988 | Spencer |
| 4,747,831 A | 5/1988 | Kulli |
| 4,828,548 A | 5/1989 | Walter |
| 4,832,696 A | 5/1989 | Luther et al. |
| 4,871,355 A | 10/1989 | Kikkawa |
| 4,887,998 A | 12/1989 | Martin et al. |
| 4,911,693 A | 3/1990 | Paris |
| 4,923,447 A | 5/1990 | Morgan |
| 4,927,416 A | 5/1990 | Tomkiel |
| 4,929,237 A | 5/1990 | Medway |
| 4,931,040 A | 6/1990 | Haber et al. |
| 4,943,282 A | 7/1990 | Page et al. |
| 4,966,592 A | 10/1990 | Burns et al. |
| 4,986,819 A | 1/1991 | Sobel |
| 5,026,349 A | 6/1991 | Schmitz et al. |
| 5,106,379 A | 4/1992 | Leap |
| 5,108,378 A | 4/1992 | Firth et al. |
| 5,112,307 A | 5/1992 | Haber et al. |
| 5,141,500 A | 8/1992 | Hake |
| 5,163,918 A * | 11/1992 | Righi et al. ............... 604/198 |
| 5,201,708 A | 4/1993 | Martin |
| 5,201,720 A | 4/1993 | Borgia et al. |
| 5,261,880 A | 11/1993 | Streck et al. |
| 5,267,972 A | 12/1993 | Anderson |
| 5,279,581 A | 1/1994 | Firth et al. |
| 5,346,480 A | 9/1994 | Hess et al. |
| 5,360,410 A | 11/1994 | Wacks |
| 5,380,296 A | 1/1995 | Smedley et al. |
| 5,411,487 A | 5/1995 | Castagna |
| 5,501,672 A | 3/1996 | Firth et al. |
| 5,531,706 A | 7/1996 | de la Fuente |
| 5,558,651 A | 9/1996 | Crawford et al. |
| 5,573,513 A | 11/1996 | Wozencroft |
| 5,591,138 A | 1/1997 | Vaillancourt |
| 5,601,536 A | 2/1997 | Crawford et al. |
| 5,803,918 A | 9/1998 | Vetter et al. |
| 5,817,064 A | 10/1998 | DeMarco et al. |
| 5,855,580 A | 1/1999 | Brunel |
| 5,891,104 A | 4/1999 | Shonfeld et al. |
| 5,891,105 A | 4/1999 | Mahurkar |
| 5,913,846 A | 6/1999 | Szabo |
| 5,989,226 A | 11/1999 | Hymanson |
| 5,997,513 A | 12/1999 | Smith et al. |
| 6,013,059 A | 1/2000 | Jacobs |
| 6,033,386 A | 3/2000 | Novacek et al. |
| 6,086,566 A | 7/2000 | Amissolle |
| 6,159,184 A | 12/2000 | Perez et al. |
| 6,171,284 B1 | 1/2001 | Kao et al. |
| 6,186,980 B1 | 2/2001 | Brunel |
| 6,296,625 B1 | 10/2001 | Vetter et al. |
| 6,319,233 B1 | 11/2001 | Jansen et al. |
| 6,344,032 B1 | 2/2002 | Perez et al. |
| 6,416,323 B1 | 7/2002 | Grenfell et al. |
| 6,419,658 B1 * | 7/2002 | Restelli et al. ............. 604/110 |
| 6,475,194 B2 | 11/2002 | Domici, Jr. et al. |
| 6,547,764 B2 | 4/2003 | Larsen et al. |
| 6,565,540 B1 | 5/2003 | Perouse et al. |
| 6,569,115 B1 | 5/2003 | Barker et al. |
| 6,585,702 B1 | 7/2003 | Brunel |
| 6,613,022 B1 | 9/2003 | Doyle |
| 6,623,459 B1 | 9/2003 | Doyle |
| 6,685,676 B2 | 2/2004 | Jansen et al. |
| 6,719,730 B2 | 4/2004 | Jansen et al. |
| 6,918,889 B1 | 7/2005 | Brunel |
| 6,949,086 B2 | 9/2005 | Ferguson et al. |
| 6,966,898 B1 | 11/2005 | Pouget et al. |
| 6,997,901 B2 | 2/2006 | Popovsky |
| 7,029,461 B2 | 4/2006 | Ferguson et al. |
| 7,097,636 B2 | 8/2006 | Pessin |
| 7,144,389 B2 | 12/2006 | Ferguson et al. |
| 7,300,421 B1 | 11/2007 | Lowry et al. |
| 7,429,256 B2 | 9/2008 | Chevallier et al. |
| 7,582,073 B2 | 9/2009 | Barrelle et al. |
| 7,678,086 B2 | 3/2010 | Chevallier |
| 7,699,814 B2 | 4/2010 | Lande |
| 7,824,379 B2 | 11/2010 | Doyle |
| 7,875,006 B2 | 1/2011 | Pessin |
| 7,938,808 B2 | 5/2011 | Pessin |
| 8,118,787 B2 | 2/2012 | Chevallier et al. |
| 8,192,407 B2 | 6/2012 | Pessin |
| 2001/0031949 A1 | 10/2001 | Asbaghi |
| 2001/0039401 A1 | 11/2001 | Ferguson et al. |
| 2002/0002354 A1 | 1/2002 | Vetter et al. |
| 2002/0045864 A1 | 4/2002 | Perez et al. |
| 2002/0068921 A1 | 6/2002 | McWethy et al. |
| 2002/0156426 A1 | 10/2002 | Gagnieux et al. |
| 2002/0161337 A1 * | 10/2002 | Shaw et al. ................ 604/197 |
| 2002/0193746 A1 * | 12/2002 | Chevallier ................. 604/197 |
| 2003/0050607 A1 | 3/2003 | Gagnieux et al. |
| 2003/0229314 A1 | 12/2003 | McWethy et al. |
| 2004/0015137 A1 | 1/2004 | Hohlfelder et al. |
| 2004/0144668 A1 | 7/2004 | Marshall et al. |
| 2004/0193120 A1 | 9/2004 | Ferguson et al. |
| 2004/0236283 A1 * | 11/2004 | Tang ........................... 604/197 |
| 2004/0267206 A1 | 12/2004 | Rimlinger et al. |
| 2005/0020985 A1 | 1/2005 | Doyle |
| 2005/0080383 A1 | 4/2005 | Woehr |
| 2005/0119623 A1 | 6/2005 | Pessin |
| 2005/0148933 A1 | 7/2005 | Raven et al. |
| 2005/0148943 A1 | 7/2005 | Chevalier |
| 2005/0165353 A1 | 7/2005 | Pessin |
| 2006/0184133 A1 | 8/2006 | Pessin |
| 2006/0200077 A1 * | 9/2006 | Righi et al. ................. 604/110 |
| 2006/0264887 A1 | 11/2006 | Lande |
| 2007/0088287 A1 | 4/2007 | Chevallier |
| 2007/0239117 A1 | 10/2007 | Chelak et al. |
| 2008/0021409 A1 | 1/2008 | Pessin |
| 2008/0208140 A1 | 8/2008 | Barrelle |
| 2008/0294120 A1 | 11/2008 | Chevallier et al. |
| 2008/0312603 A1 | 12/2008 | Chevallier et al. |
| 2009/0105661 A1 | 4/2009 | Chevallier et al. |
| 2010/0217205 A1 | 8/2010 | Chevallier et al. |
| 2012/0022465 A1 | 1/2012 | Stamp et al. |
| 2012/0095408 A1 | 4/2012 | Eaton et al. |
| 2014/0121605 A1 | 5/2014 | Feret et al. |
| 2014/0163476 A1 | 6/2014 | Chevallier et al. |

FOREIGN PATENT DOCUMENTS

| | | |
|---|---|---|
| EP | 1 066 848 A2 | 1/2001 |
| EP | 1474194 A1 | 11/2004 |
| EP | 1532997 A1 | 5/2005 |
| EP | 1235603 B1 | 5/2006 |
| FR | 2 653 667 | 5/1991 |
| FR | 2762790 A1 | 11/1998 |
| FR | 2794650 A1 | 12/2000 |
| FR | 2807665 A1 | 10/2001 |
| FR | 2830764 A1 | 4/2003 |
| FR | 2830765 A1 | 4/2003 |
| FR | 2 835 753 | 8/2003 |
| FR | 2837107 A1 | 9/2003 |
| FR | 2860162 A1 | 4/2005 |
| FR | 2861598 A1 | 5/2005 |
| FR | 2922455 A1 | 4/2009 |
| JP | 5500621 T | 2/1993 |
| JP | H08-010324 A | 1/1996 |
| JP | 9502893 T | 3/1997 |
| JP | 2843677 B2 | 1/1999 |
| JP | 11319090 A | 11/1999 |
| JP | 2003-501218 A | 1/2003 |
| JP | 2003-511106 A | 3/2003 |
| JP | 2004528075 T | 9/2004 |
| JP | 2005-516741 T | 6/2005 |
| JP | 2006-505340 A | 2/2006 |
| WO | 9426334 A1 | 11/1994 |

(56) References Cited

FOREIGN PATENT DOCUMENTS

| WO | WO 98/35714 | | 8/1998 | |
|---|---|---|---|---|
| WO | 99 17823 | A1 | 4/1999 | |
| WO | 0124856 | A1 | 4/2001 | |
| WO | 0130427 | A1 | 5/2001 | |
| WO | 0137898 | A2 | 5/2001 | |
| WO | 0141841 | A2 | 6/2001 | |
| WO | 0185239 | A2 | 11/2001 | |
| WO | WO 02/72182 | * | 9/2002 | ............. A61M 5/50 |
| WO | WO 02/72182 | A1 | 9/2002 | |
| WO | 02089878 | A1 | 11/2002 | |
| WO | 03068298 | A1 | 8/2003 | |
| WO | 03/077977 | A2 | 9/2003 | |
| WO | 2004043524 | A1 | 5/2004 | |
| WO | 2004087242 | A1 | 10/2004 | |
| WO | 2005039678 | A2 | 5/2005 | |
| WO | 2006/027445 | A1 | 3/2006 | |

OTHER PUBLICATIONS

Office Action issued Sep. 14, 2010 in Japanese Patent Application No. 2006-536115.
Japanese Office Action mailed Mar. 16, 2010 in JP Appln No. 2006-537346.
Int'l Search Report and Written Opinion issued Dec. 22, 2011 in Int'l Application PCT/US2011/031053.
Office Action issued Mar. 28, 2007 in U.S. Appl. No. 10/550,524.
Int'l Search Report issued Sep. 22, 2004 in Int'l Application No. PCT/FR2004/000755.
Office Action issued Apr. 17, 2009 in U.S. Appl. No. 11/861,567.
Office Action issued Jan. 13, 2010 in U.S. Appl. No. 11/861,567.
Office Action issued Sep. 1, 2009 in JP Application No. 2006-505752.
Office Action issued Jun. 8, 2010 in JP Application No. 2006-505752.
Office Action issued Dec. 7, 2010 in JP Application No. 2006-505752.
Search Report Issued Jul. 9, 2009 in EP Application No. 08 166 632.3.
Search Report Issued Jun. 13, 2008 in FR Application No. 0758496.
Office Action issued Mar. 22, 2011 in U.S. Appl. No. 12/738,509.
Office Action issued Aug. 25, 2011 in U.S. Appl. No. 12/738,509.
Int'l Search Report issued May 11, 2009 in Int'l Application No. PCT/FR2008/051908; Written Opinion.
Search Report issued Jun. 17, 2008 in FR Application No. 0758497; Written Opinion.
Office Action issued Dec. 23, 2011 in CN Application No. 200880112730.3.
Int'l Preliminary Report on Patentability issued Oct. 8, 2013 in Int'l Application No. PCT/US2011/031053.
Office Action issued Dec. 18, 2006 in U.S. Appl. No. 10/507,913 by Pessin.
Office Action issued Sep. 7, 2007 in U.S. Appl. No. 10/507,913 by Pessin.
Office Action issued Dec. 17, 2008 in U.S. Appl. No. 10/507,913 by Pessin.
Office Action issued Oct. 8, 2009 in U.S. Appl. No. 10/507,913 by Pessin.
Office Action issued Apr. 23, 2009 in EP Application No. 04 818 444.4.
Office Action issued Nov. 23, 2010 in EP Application No. 04 818 444.4.
Office Action issued Apr. 17, 2013 in EP Application No. 04 818 444.4.
Search Report and English translation of Written Opinion issued Jul. 9, 2009 in EP Application No. 08 166 632.3.
Office Action issued Apr. 21, 2005 in U.S. Appl. No. 10/995,035 by Pessin.
Office Action issued Oct. 5, 2005 in U.S. Appl. No. 10/995,035 by Pessin.
Office Action issued Sep. 28, 2010 in JP Application No. 2007-528015.

Office Action issued Sep. 6, 2011 in JP Application No. 2007-528915.
Int'l Search Report issued Jan. 3, 2006 in Int'l Application No. PCT/FR2005/001983.
Int'l Preliminary Report on Patentability issued Feb. 28, 2007 in Int'l Application No. PCT/FR2005/01983.
Int'l Search Report issued Jan. 25, 2006 in Int'l Application No. PCT/FR2005/001926.
Int'l Preliminary Report on Patentability issued Feb. 28, 2007 in Int'l Application No. PCT/FR2005/001926.
Office Action issued May 15, 2009 in U.S. Appl. No. 11/574,333 by Pessin.
Office Action issued Sep. 10, 2008 in U.S. Appl. No. 11/574,333 by Pessin.
Office Action issued Dec. 13, 2007 in U.S. Appl. No. 11/574,333 by Pessin.
Office Action issued Aug. 20, 2010 in U.S. Appl. No. 11/574,176 by Pessin.
Int'l Preliminary Report on Patentability issued Feb. 21, 2006 in Int'l Application No. PCT/FR2004/000755.
Search Report issued Mar. 4, 2004 in FR Application No. 0312642.
Int'l Search Report issued Apr. 4, 2006 in Int'l Application No. PCT/FR2004/002597.
Office Action issued Mar. 11, 2009 in U.S. Appl. No. 10/577,380 by Chevallier.
Office Action issued Feb. 16, 2012 in CN Application No. 200880112413.1.
Int'l Search Report and Written Opinion issued May 11, 2009 in Int'l Application No. PCT/FR2008/051907.
Int'l Preliminary Report on Patentability issued Jun. 1, 2010 in Int'l Application No. PCT/FR2008/051907.
Office Action issued Mar. 22, 2011 in U.S. Appl. No. 12/738,422.
Office Action issued Aug. 18, 2011 in U.S. Appl. No. 12/738,422.
Office Action issued Jul. 1, 2009 in U.S. Appl. No. 12/254,266 by Chevallier.
Office Action issued Feb. 4, 2010 in U.S. Appl. No. 12/254,266 by Chevallier.
Office Action issued Nov. 3, 2011 in U.S. Appl. No. 12/254,266 by Chevallier.
Office Action issued Apr. 23, 2012 in U.S. Appl. No. 12/254,266 by Chevallier.
Office Action issued May 10, 2013 in U.S. Appl. No. 12/254,266 by Chevallier.
Office Action issued Oct. 10, 2013 in U.S. Appl. No. 12/254,266 by Chevallier.
Search Report issued Jun. 24, 2004 in FR application No. 0312327.
Office Action issued Sep. 28, 2010 in JP Application No. 2007-528913.
Search Report issued Feb. 22, 2005 in EP Application No. 04 29 2750.
Office Action issued Nov. 28, 2006 in EP Application No. 04 292 750.
Office Action issued Mar. 11, 2008 in EP Applicaton No. 04 292 750.
Office Action issued Sep. 11, 2009 in EP Application No. 05 792 448.
Int'l Preliminary Report on Patentability issued Dec. 12, 2013 in Int'l Application No. PCT/US2012/039385.
Japanese Office Action for the related Japanese Application No. 2006-536115 mailed Feb. 2, 2010.
Preliminary Search Report for the related French Application No. 0312327 dated Jun. 21, 2004.
International Search Report and Written Opinion for the related International Application No. PCT/FR2004/002654 mailed Jun. 6, 2005.
European Office Action for the related European Application No. 04817285.2 dated Dec. 22, 2008.
International Preliminary Report on Patentability for the related International Application No. PCT/FR2004/002654 issued Jul. 27, 2006.
Int'l Search Report issued Dec. 12, 2012 in Int'l Application PCT/US2012/039385.
Office Action issued Jul. 18, 2014 in U.S. Appl. No. 14/009,814 by Chevalier.
Int'l Search Report issued Sep. 11, 2003 in Int'l Application No. PCT/FR2003/000722.

(56) References Cited

OTHER PUBLICATIONS

Search Report and Written Opinion issued Jun. 13, 2008 in FR Application No. 0758495.
Int'l Preliminary Report on Patentability issued Jun. 1, 2010 in Int'l Application No. PCT/FR2008/051908.
Int'l Preliminary Report on Patentability issued Oct. 17, 2013 in Int'l Application No. PCT/US2011/031053.
Office Action issued Jun. 24, 2014 in U.S. Appl. No. 12/738,509 by Chevalier.
Office Action issued Dec. 3, 2014 in U.S. Appl. No. 12/738,509 by Chevalier.

* cited by examiner

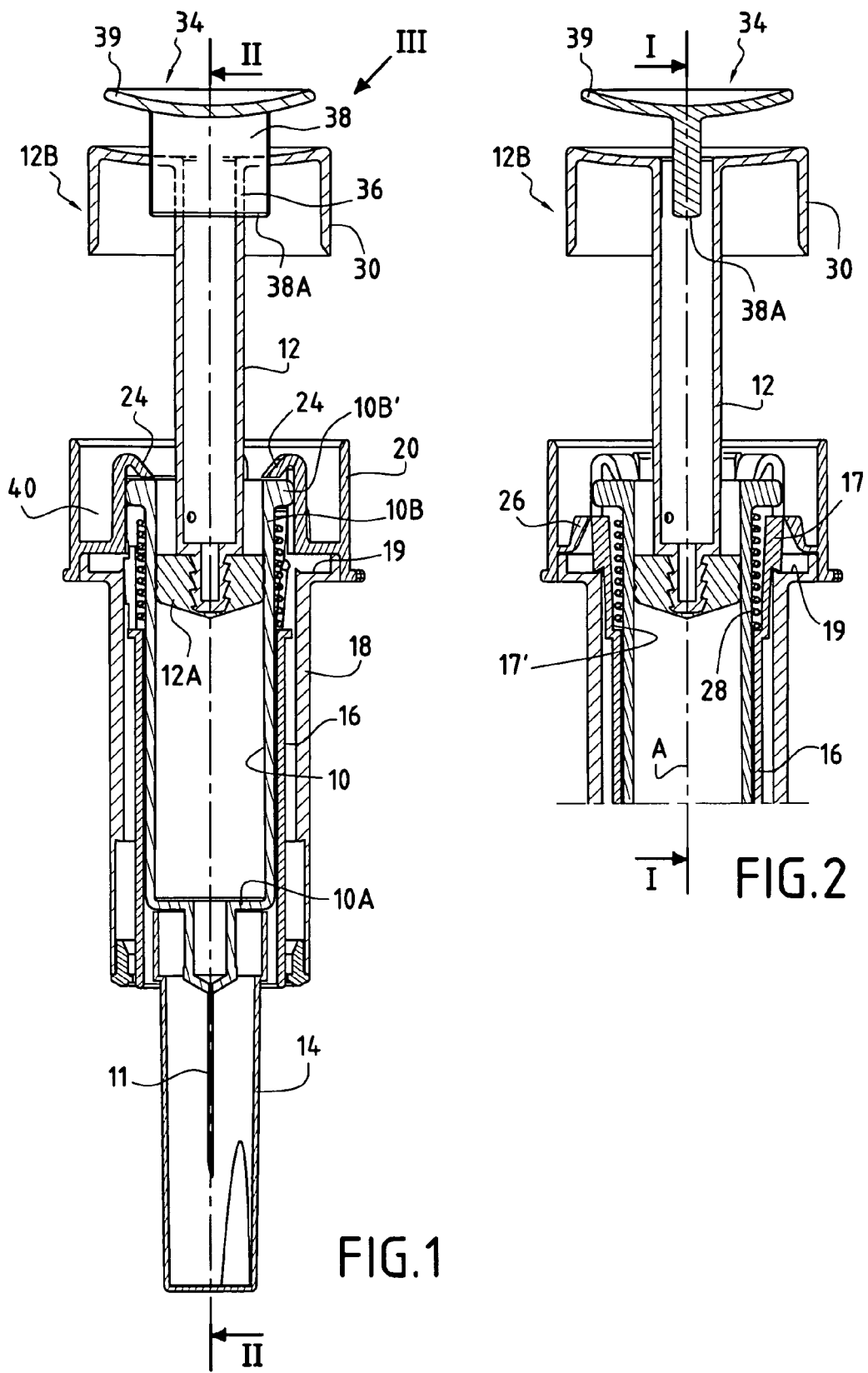

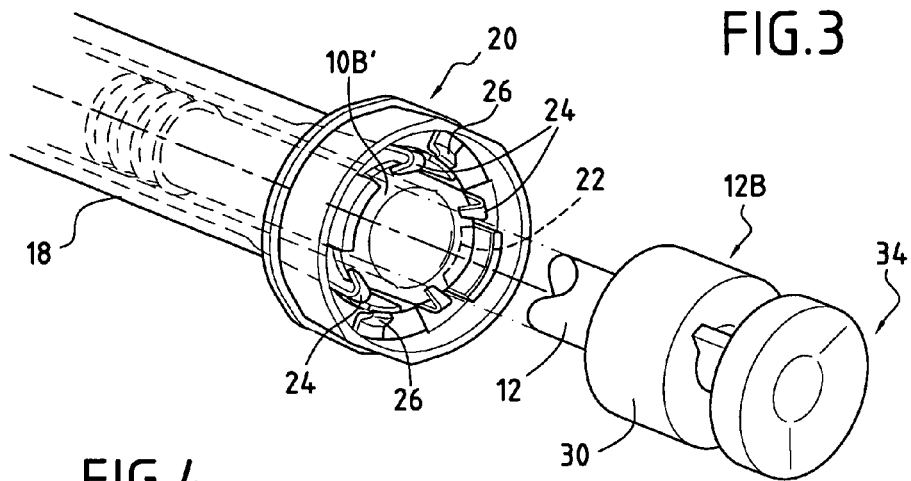
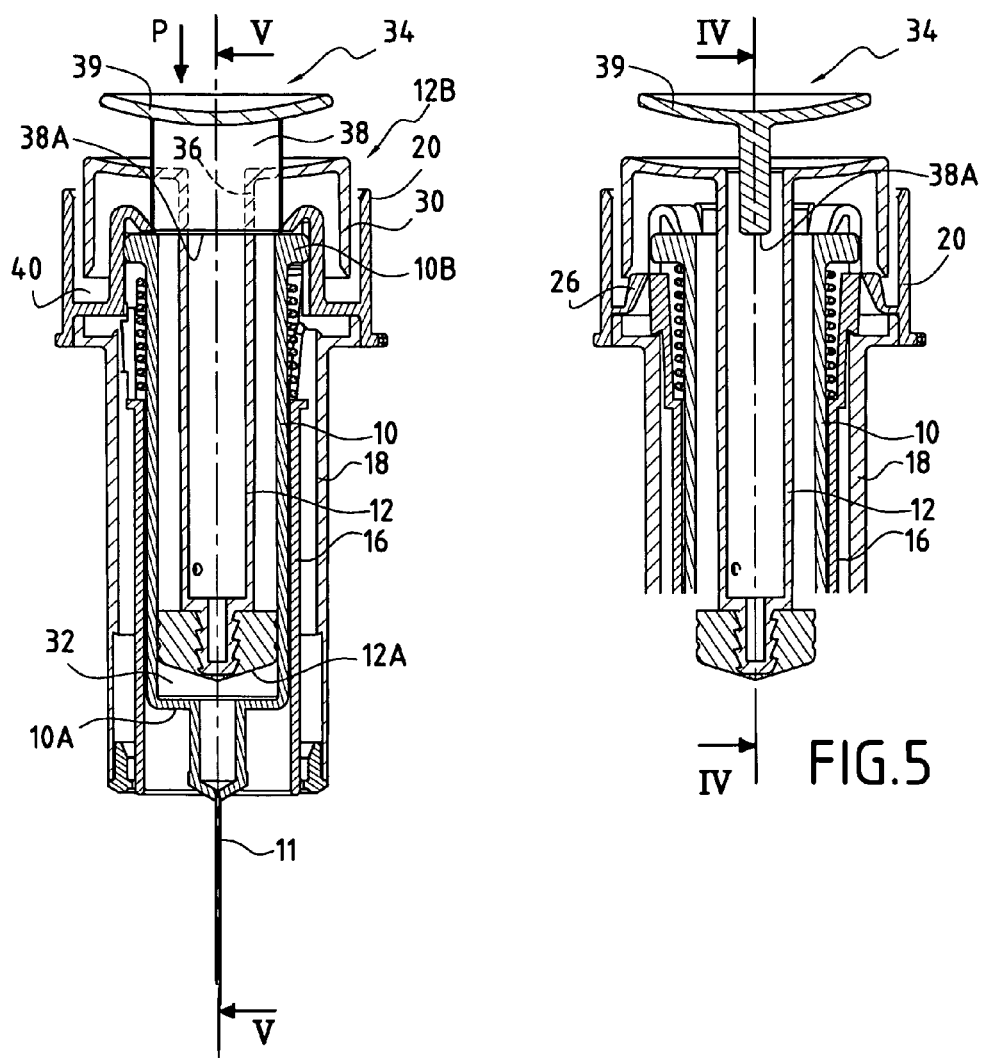

FIG.7
FIG.8
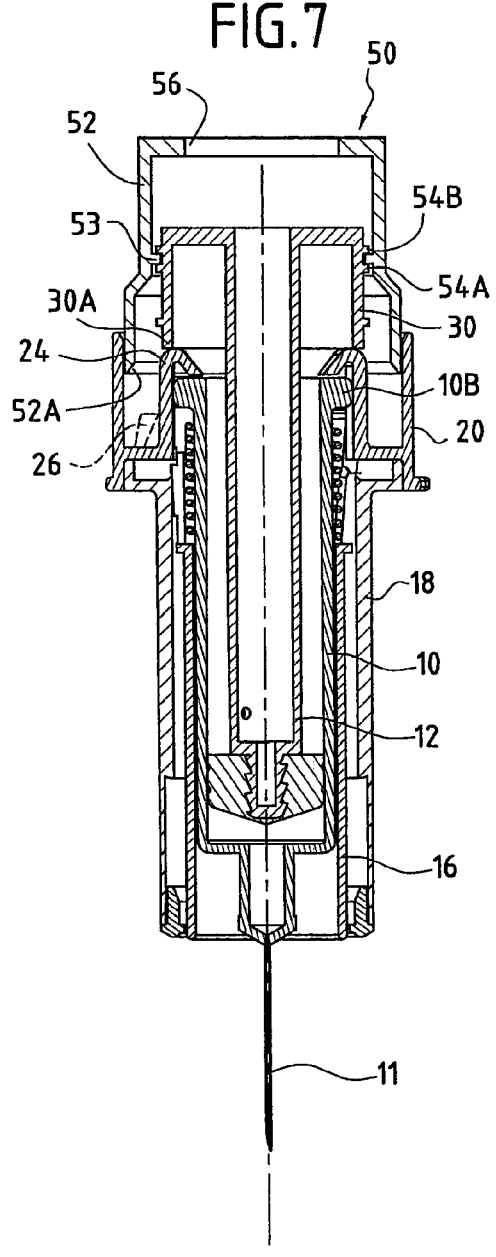
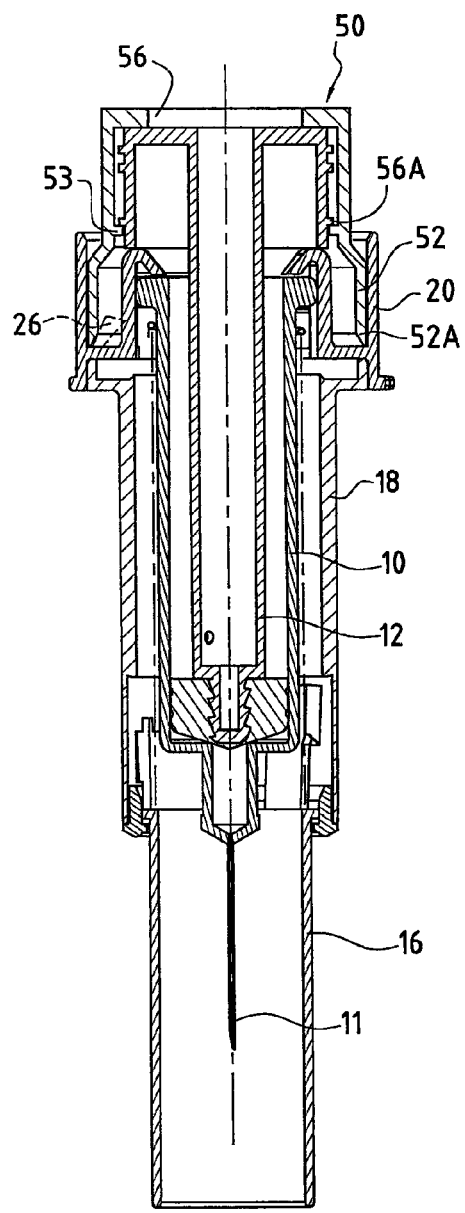

PROTECTED INJECTION SYRINGE DEVICE

This is a 371 national phase application of PCT/FR2004/002654 filed 18 Oct. 2004, claiming priority to French Patent Application No. FR 0312327 filed 22 Oct. 2003, the contents of which are incorporated herein by reference.

The present invention relates to a safe injection device comprising a syringe having a syringe body, a needle, and a piston suitable for moving in the body to perform an injection, and safety means comprising a protective sheath, the syringe body and the protective sheath being suitable for sliding relative to each other between an injection configuration in which the needle projects beyond the protective sheath which is disposed around the syringe body, and a protection configuration in which the needle extends inside said sheath, the device including a trigger member suitable for causing the device to pass from the injection configuration to the protection configuration at the end of the injection stroke.

Devices of this type are known, e.g. from patent documents FR 2 801 795, EP 0 966 983, or also EP 0 740 942.

In order to inject the liquid contained in the syringe body into the body of a patient, the syringe body and the protective sheath need to be in their injection configuration. After injection, the trigger member serves to cause them to pass into the protection configuration so as to avoid the user being accidentally pricked by the needle, thereby consequently limiting any risk of contamination.

The Applicant company has found that situations exist in which it is desirable to prevent the device taking up its injection configuration at the end of the injection stroke. This applies for example when such a device is used with a syringe that is not prefilled, and that needs to be manipulated prior to injection. In order to fill such a syringe, it is necessary for the piston to be placed at the end of its forward stroke, and then starting from said situation, for the piston to be moved rearwards, i.e. away from the needle, so that the liquid for injection penetrates into the body of the syringe. It is then appropriate, during such filling and during the following injection, for the syringe body and the protective sheath to remain in their injection configuration.

An object of the present invention is to provide a safe injection device of the above-specified type in which passage into the protection configuration is triggered at the end of the injection stroke, but not necessarily at the end of any injection stroke.

This object is achieved by the fact that the device of the invention includes means for defining a first end-of-injection-stroke situation in which the trigger member is unable to cause the device to pass from the injection configuration to the protection configuration, and a second end-of-injection-stroke situation in which the trigger member is able to cause the device to pass from the injection configuration to the protection configuration.

During manipulation of the syringe prior to injection, if any, it is the first end-of-injection-stroke situation that is defined so as to prevent the device passing in untimely manner into the protection configuration, whereas it is the second end-of-injection-stroke situation that is defined during an injection.

Advantageously, the device further comprises an inhibitor member suitable for occupying an inhibit position in which the end-of-injection-stroke situation is said first situation, and suitable for being moved relative to this inhibit position so as to enable the end-of-injection-stroke situation to be said second situation.

This inhibitor member preferably constitutes a part that is easily manipulated, and that is initially in its inhibit position.

In a first advantageous embodiment, the trigger member is constrained to move with the piston, and the device includes means for defining first and second end-of-injection-stroke positions for the piston that correspond respectively to the first and second end-of-injection-stroke situations.

Preferably, provision is made for the two end-of-injection-stroke positions of the piston to be close to each other, so that in both positions the syringe body contains no air or liquid, or hardly any.

Under such circumstances, and advantageously, the device includes abutment means suitable for being put into operation to define the first end-of-injection-stroke position, and for being taken-out of operation in order to enable the second end-of-injection-stroke-position to be reached.

When these abutment means are in operation, they define the first end-of-injection-stroke position for the piston, in which the front end of the piston is situated close to the front end of the syringe body where the needle is located, but without nevertheless reaching said front end. In contrast, when the abutment means are out of operation, the front end of the piston can go a little way beyond said first end-of-injection-stroke position.

Advantageously, in its inhibit position, the inhibitor member is connected to the piston, being constrained to move together therewith, and is suitable for co-operating in abutment with an element of the device that is stationary relative to the syringe body in order to define the first end-of-injection-stroke position.

Since the inhibitor member is initially in its inhibit position, the first end-of-injection-stroke position is automatically obtained by pushing the piston forwards until the inhibitor member comes into abutment. In order to enable the second end-of-injection-stroke position to be reached, it suffices to move the inhibitor member, either by moving it rearwards relative to the piston, or for example by separating it from the piston, so that at the end of injection into the body of a patient, the piston can reach its second end-of-injection-stroke position.

In a second advantageous embodiment, the trigger member is connected to the piston and is suitable for being moved relative thereto between a position that is suitable for triggering in which, at the end of the injection stroke of the piston, said trigger member is suitable for causing the device to pass from the injection configuration to the protection configuration, and a position that is not suitable for triggering, in which, at the end of the injection stroke of the piston, the trigger member is unsuitable for causing the device to pass from the injection configuration to the protection configuration.

Under such circumstances, the trigger member is placed in its position that is unsuitable for triggering while performing manipulations on the device prior to making an injection. Once these manipulations have been completed, with the syringe then being ready for injection, the trigger member can be placed in its position that is suitable for triggering so that the protection configuration is reached at the end of injection.

Under such circumstances, and advantageously, the trigger member is movable axially relative to the piston, the position suitable for triggering being offset towards the end of the piston that is directed towards the needle relative to the position that is unsuitable for triggering.

The invention can be well understood and its advantages can be seen better on reading the following detailed description of embodiments given as non-limiting examples. The description refers to the accompanying drawings, in which:

FIG. 1 is a view of a device in accordance with the invention, shown in longitudinal section, with the syringe body and the protective sheath being shown in their injection configuration;

FIG. 2 is a fragmentary view of the FIG. 1 device, in section on line II-II of FIG. 1;

FIG. 3 is a fragmentary perspective view of the device seen from behind, looking along arrow III in FIG. 1;

FIGS. 4 and 5 are views analogous to FIGS. 1 and 2, showing the first end-of-injection-stroke situation, with FIG. 5 being a fragmentary section;

FIG. 7 is a view analogous to FIG. 4, for a second embodiment; and

FIG. 8 is a view analogous to FIG. 6, for the second embodiment.

Figure 6:
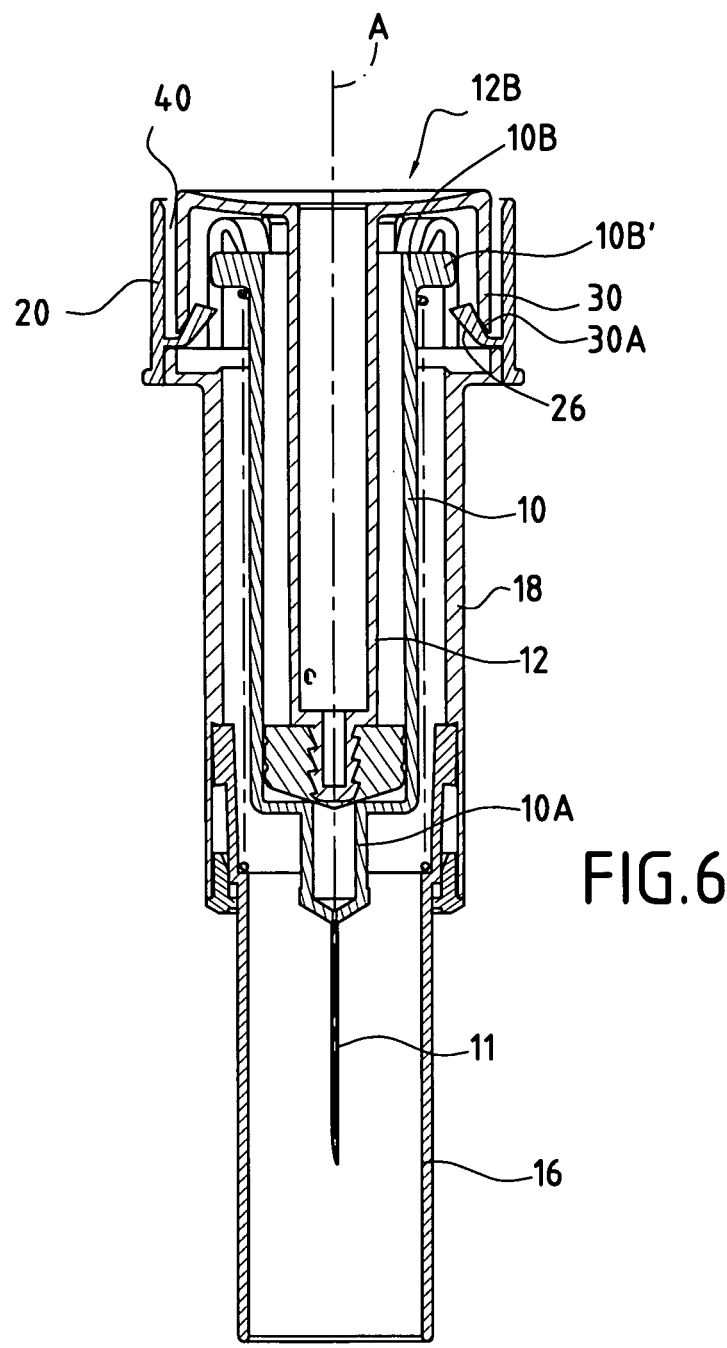
FIG. 6 is a view in the same section plane as FIGS. 2 and 5, showing the section end-of-injection-stroke situation, and the protection configuration.

The device shown in the figures comprises a syringe having a syringe body 10, a needle 11, and a piston 12 capable of sliding in the body to make an injection. In FIGS. 1 and 2, the piston 12 is in its injection-ready position, in which its front end 12A is situated towards the rear end 10B of the syringe body 10, i.e. the end that is remote from the needle.

The device is shown prior to injection, and in conventional manner, the needle 11 is protected by a protective cap 14 that is fitted onto the front end 10A of the syringe body 10.

The device also comprises safety means comprising a protective sheath 16.

In FIGS. 1 to 5 and 7, the protective sheath 16 is in a ready position in which it is disposed around the syringe body 10; this is the injection configuration. In FIGS. 6 and 8, displacement of the sheath relative to the syringe body 10 has been triggered, and it can be seen that the sheath 16 projects beyond the front end 10A of the syringe body, such that the needle 11 extends inside the sheath; this is the protection configuration.

In the example shown, the protection means are analogous to those disclosed in patent document FR 2 801 795, and at the end of injection, it is the sheath 16 that moves relative to the syringe body so as to advance and come into place around the needle.

More precisely, the syringe body is placed in a support sheath 18 inside which the protective sheath 16 is retracted when in the ready position, being placed in an annular space that extends between the syringe body and the support sheath.

The rear end of the support sheath 18 is formed by an end portion 20 that enables the syringe body to be held in stationary manner inside the support sheath by a collar 10B' at said rear end. More precisely, as can be seen in FIG. 3, the portion 20 presents radial wall elements 22 forming shoulder portions facing rearwards and on which the collar 10B' rests in such a manner as to prevent the syringe body from moving forwards relative to the support sheath. The portion 20 also includes retaining tongues 24 that are resilient and that splay out radially while the collar 10B' is being inserted into the portion 20 as far as the shoulder portions 22, prior to returning to their initial position in order to retain the collar against rearward displacement.

Furthermore, the rear end of the sheath 18 presents a rearwardly-directed inside shoulder 19 in its zone where it connects with the portion 20, with resilient tabs 17 at the rear end of the protective sheath 16 engaging on said shoulder in the injection configuration in order to prevent the protective sheath from moving forwards.

The portion 20 presents actuator tabs 26 which are situated facing the tabs 17, as can be seen in FIG. 2.

In the vicinity of its rear end, the protective sheath 16 presents a step 17' forming a rearwardly-facing inside shoulder for the front end of a spring 28. The rear end of the spring rests against the front face of wall elements that constitute the above-described shoulder portions 22. Thus, in the injection configuration, the spring 28 is compressed.

The rear head 12B of the piston 12 presents a skirt 30 that constitutes a trigger member for causing the device to pass into its protection configuration.

As can be seen in FIG. 6, when the piston 12 is fully advanced inside the syringe body 10, the front end 30A of the skirt co-operates with the resilient tabs 26 to push them radially inwards, i.e. towards the axis A of the device, such that these tabs push away the tabs 17 of the protective sheath, likewise inwards. As a result, the sheath is no longer retained by the shoulder 19 and it can advance under the thrust from the spring 28 so as to reach the position shown in FIG. 6, in which the device is in its protection configuration.

The above-described safety means correspond to those defined in patent document FR 2 801 795, and the syringe body is stationary, while it is the protective sheath that advances relative thereto in order to obtain the protection configuration. Naturally, the invention also applies to inverse devices in which it is the syringe body that moves rearwards relative to the protective sheath in order to define the protection configuration.

In both circumstances, the protection configuration is obtained at the end of the injection stroke.

The device of the invention includes means for defining two distinct situations at the end of the injection stroke, one in which triggering of the injection configuration does not take place, and the other in which said triggering does take place.

In the example of FIGS. 1 to 6, the trigger member constituted by the skirt 30 is constrained to move with the piston 12, and the first and second end-of-injection-stroke situations correspond respectively to first and second positions for the piston at the end of the injection stroke.

The first end-of-injection-stroke position is shown in FIGS. 4 and 5, and it can be seen that the front end 12A of the piston 12 does not quite come into contact with the front end 10A of the syringe body. The gap 32 that is left between these two ends is exaggerated in the drawing in order to improve understanding of the invention. Nevertheless, this gap presents a volume that is very small, and provision can even be made, in this first end-of-stroke position, for the front end of the piston to come into contact with the wall formed at the front 10A of the syringe body, since this front end E of the piston is formed by a flexible part, e.g. made of elastomer, presenting deformability that enables it to be compressed a little so that in the second end-of-stroke configuration, the piston can advance further forwards in order to occupy its second end-of-stroke position, as shown in FIG. 6.

In the first embodiment, the device includes an inhibitor member 34 which, in FIGS. 1 to 5, is shown in its inhibit position in which it is connected to the head 12B of the piston 12. In the example shown, the inhibitor member 34 is formed by a head part 34 fitted on the head 12B of the piston in its inhibit position and that can be separated from said head in order to enable the piston to reach its second end-of-injection-stroke position. More precisely, in its inhibit position shown in FIGS. 1 to 5, the inhibitor member 34 passes through the piston head which presents a slot 36 for this purpose. It is a longitudinal portion of the part 34 formed by a tenon or by a wall element 38 that passes through this slot. The front end 38A of the tenon or wall element is thus located in a space inside the head of the piston, which space is formed between the inside face of the skirt 30 and the rod of the piston. In the inhibit position of the part 34, the tenon 38 advances towards the end of the piston remote from its head 12B, further than the skirt 30.

As can be seen in FIG. 4, the front end 38A of the wall element 38 of the inhibitor member 34 comes into abutment against the rear end 10B of the syringe body 10 in order to define the first end-of-injection-stroke position. In order to move the piston forwards, the user naturally presses on the inhibitor member 34, or more precisely on the actuator head 39 of said member. It will be understood that in the position of FIG. 4, any thrust P applied to said head 39 has no further effect.

It should be observed that in order to define the first end-of-injection-stroke position, the inhibitor member could co-operate in abutment with an element of the device other than the rear end of the syringe body. It could co-operate with any element that is stationary relative to the syringe body, and in particular with any suitable portion of the outer sheath 18 or of the portion 20.

In the embodiment of FIGS. 1 to 6, in order to enable the second end-of-stroke position to be reached, it suffices to separate the inhibitor member 34 from the piston head. This is shown in FIG. 6, where the inhibitor member is removed, thus enabling the skirt 30 to come into contact with the actuator tabs 26, as is not possible in the preceding figures.

Without going beyond the ambit of the invention, the shape of the piston head and of the inhibitor member could be modified so that starting from its inhibit position, the inhibitor member can be moved rearwards relative to the head in such a manner that its front end 38A is set back, so that it no longer comes into abutment against the rear end of the syringe body at the end of injection, thus making it possible to reach the second end-of-stroke position. In order to retain the inhibitor member in this set-back position, it could be made to co-operate with the piston head by means of a bayonet system or the equivalent, for example.

As can be seen in FIG. 6, in the example shown, the space inside the portion 20 forms a housing 40 in which the head 12B of the piston is substantially retracted in the second end-of-injection-stroke position, such that the piston is no longer usable or practically no longer usable. However, in FIGS. 4 and 5, it can be seen that in the first end-of-injection-stroke position, the piston head projects beyond this housing. The user can thus obtain a purchase enabling the piston to be pulled rearwards, so as to prepare the device for making an injection.

FIGS. 7 and 8 show a second embodiment of the means that enable the first and second end-of-injection-stroke situations to be obtained, and they are described below. In these figures, the trigger member is formed by the skirt 52 of a cover 50 that is placed around the head 12B of the piston and that can be moved relative thereto.

FIG. 7 shows the cover 50 in its position that is unsuitable for triggering, in which it is set back rearwards relative to the head 12B. Thus, the front end 52A of the skirt 52 does not come into contact with the above-mentioned actuator tabs 26 at the end of the injection stroke. To clarify the explanation, an actuator tab 26 is shown in dashed lines in FIGS. 7 and 8, even though it does not lie in the section plane of these figures.

In contrast, in FIG. 8, the cover 50 has been advanced over the piston head 12B so that at the end of the injection stroke its skirt 52 can co-operate with the tongues 26 via its front end, in the same manner as the skirt 30 in the above-described embodiment shown in FIG. 6.

Advantageously, the sliding travel of the trigger member 50 relative to the piston 12 includes a hard point for holding the trigger member in its position that is unsuitable for triggering. Specifically, the inside wall of the skirt 52 presents a snap-fastening bead 53 which, in the position unsuitable for triggering as shown in FIG. 7, is held between two beads 54A and 54B formed on the outside wall of the skirt 30 of the head 12B. It should be observed that in order to enable the piston to be actuated without moving the cover 50 forwards, the rear end wall thereof presents a central opening 56 through which the user can insert a finger in order to press directly on the head 12B of the piston.

Starting from the situation shown in FIG. 7, the piston can be moved rearwards by handling the cover 50, which is retained by the bead 54B against moving rearwards.

When the piston head is moved rearwards so as to be spaced apart from the support sheath 18, the user can hold the piston rod between two fingers while using another finger to push the part 50 forwards so as to go past the above-mentioned hard point. Specifically, the outer wall of the skirt 30 presents another bead 56A situated close to its front end, with the bead 53 of the skirt 52 being located in front of it when the cover 50 is in its position suitable for triggering.

It can be seen that when the cover 50 is in its position that is unsuitable for triggering, it is the front end 30A of the skirt 30 of the piston head that prevents the piston from being moved forwards beyond its first end-of-stroke position as shown in FIG. 7, by co-operating in abutment with an element that is stationary relative to the syringe body, and specifically that is constituted by the rear ends of the tongues 24.

In the examples shown, the means (inhibitor member 54 or trigger member 50) that, in association with the piston, serve to prevent the device always passing into the end-of-injection protection configuration, are secured to the piston head and can be separated or moved relative to said head in order to enable the second end-of-injection-stroke situation to be reached. In the above two examples, these means are external to the piston, naturally, it will be possible to use a member that is internal to the piston, e.g. passing via the inside of a hollow piston rod in order to come optionally into abutment with a stationary element of the device, e.g. the collar of the syringe or an element secured to the portion 20.

The invention claimed is:

1. A safe injection device comprising
a syringe having a syringe body, a needle, and a piston suitable for moving in the body to perform an injection, the piston having a piston head at one end distal to the needle and
a support sheath disposed around the syringe body and holding the syringe body in a stationary manner,
a protective sheath disposed in an annular space between the syringe body and the support sheath and extending therebetween,
the protective sheath being displaceable relative to the syringe body and the support sheath between an injection configuration in which the needle projects beyond the protective sheath, and a protection configuration in which the needle extends inside the protective sheath,
a trigger member suitable for causing the protective sheath to slide from the injection configuration to the protection configuration at an end of an injection stroke, the trigger member being located at the piston head secured to the piston, and
an inhibitor member received within a slot of the piston head, the inhibitor member being suitable for occupying an inhibit position, wherein the piston has reached a first end-of-injection-stroke position in which the syringe body is substantially emptied of air or liquid and the trigger member is unable to cause the protective sheath to slide from the injection configuration to the protection configuration, and the inhibitor member is completely removable from the piston at said inhibit position, to enable the piston to reach a second end-of-injection-stroke position in which the trigger member is able to cause the protective sheath to slide from the injection configuration to the protection configuration, wherein in the inhibit position, the inhibitor member includes an actuator head to allow a user to advance the piston that is constrained to move therewith and configured for co-operating in abutment with an element of the device that is stationary relative to the needle to define the first end-of-injection-stroke position, and the inhibitor member is configured to be separated from the piston head to enable the second end-of-injection-stroke position to be reached.

2. A safe injection device comprising a syringe having a syringe body, a needle, and a piston suitable for moving in the body to perform an injection, the piston having a piston head at one end distal to the needle, and a support sheath disposed around the syringe body and holding the syringe body in a stationary manner, a protective sheath disposed in an annular space between the syringe body and the support sheath and extending therebetween, the protective sheath being displaceable relative to the syringe body and the support sheath between an injection configuration in which the needle projects beyond the protective sheath, and a protection configuration in which the needle extends inside the protective sheath, a trigger member suitable for causing the protective sheath to slide from the injection configuration to the protection configuration at an end of an injection stroke, the trigger member being secured to the piston at the piston head, and an inhibitor member received within a slot of the piston head, the inhibitor member being suitable for occupying an inhibit position, wherein the piston has reached a first end-of-injection-stroke position in which the syringe body is substantially emptied of air or liquid and the trigger member is unable to cause the protective sheath to slide from the injection configuration to the protection configuration, and the inhibitor member is removable from a remainder of the device while at said inhibit position to enable the piston to reach a second end-of-injection-stroke position in which the trigger member is able to cause the protective sheath to slide from the injection configuration to the protection configuration, wherein in the inhibit position, the inhibitor member includes an actuator head to allow a user to advance the piston, being constrained to move therewith and is suitable for co-operating in abutment with an element of the device that is stationary relative to the needle to define the first end-of-injection-stroke position, and the inhibitor member is configured for being displaced relative to the piston head to enable the second end-of-injection-stroke position to be reached.

3. A safe injection device comprising a syringe having a syringe body, a needle, and a piston suitable for moving in the body to perform an injection, the piston having a piston head at one end distal to the needle, and a support sheath disposed around the syringe body and holding the syringe body in a stationary manner, a protective sheath disposed in an annular space between the syringe body and the support sheath and extending therebetween, the protective sheath being displaceable relative to the syringe body and the support sheath between an injection configuration in which the needle projects beyond the protective sheath, and a protection configuration in which the needle extends inside the protective sheath, a trigger member secured to the piston and positioned at the piston head for causing the protective sheath to slide from the injection configuration to the protection configuration at an end of an injection stroke, an inhibitor member including an actuator head, the inhibitor member being received within a slot of the piston head and occupying an inhibit position, the inhibitor member defining a first end-of-injection-stroke situation in which the trigger member is unable to cause the device to pass from the injection configuration to the protection configuration, and a second end-of-injection-stroke situation in which the trigger member is able to cause the device to pass from the injection configuration to the protection configuration, the trigger member being constrained to move with the piston, and said first and second end-of-injection-stroke situations corresponding respectively to first and second end-of-injection-stroke positions for the piston, the inhibitor member remaining in a fixed position until occurrence of the first end-of-injection-stroke situation, and a housing in which the piston head is substantially retracted in the second end-of-injection-stroke position, whereas, in the first end-of-injection-stroke position, the piston head projects beyond said housing to provide a purchase enabling the piston to be pulled away from the needle.

4. A device according to claim 3, wherein the inhibitor member is suitable for being moved relative to said inhibit position to define said second end-of-injection-stroke situation.

5. A device according to claim 3, wherein in the inhibit position, the inhibitor member is connected to the piston being constrained to move therewith, and is suitable for co-operating in abutment with an element of the device that is stationary relative to the needle in order to define the first end-of-injection-stroke position.

6. A device according to claim 5, wherein the inhibitor member is suitable for being separated from the piston, in order to enable the second end-of-injection-stroke position to be reached.

7. A device according to claim 5, wherein the inhibitor member is suitable for being displaced relative to the piston, in order to enable the second end-of-injection-stroke position to be reached.

8. A device according to claim 5, wherein the trigger member is located at the piston head, and the inhibitor member is connected to said piston head in the inhibit position.

9. A device according to claim 8, wherein, in the inhibit position, the inhibitor member extends into the piston head.

10. A safe injection device comprising a syringe having a syringe body, a needle, and a piston suitable for moving in the body to perform an injection, the piston having a head that includes a slot, and a support sheath disposed around the syringe body and holding the syringe body in a stationary manner, a protective sheath disposed in an annular space between the syringe body and the support sheath and extending therebetween, the protective sheath being displaceable relative to the syringe body and the support sheath between an injection configuration in which the needle projects beyond the protective sheath, and a protection configuration in which the needle extends inside the protective sheath, a trigger member suitable for causing the protective sheath to slide from the injection configuration to the protection configuration at an end of an injection stroke, the trigger member being formed by a skirt secured to the piston at the piston head, an inhibitor member formed by a part that, in an inhibit position, is removably fitted on the head of the piston and received within the slot of the head of the piston and presents an end suitable for coming into abutment against an element that is stationary relative to the needle in order to define a first end-of-injection-stroke position for the piston in which the skirt is unable to cause the device to pass from the injection configuration to the protection configuration, and that is suitable for being separated from the piston in order to enable a second end-of-injection-stroke position of the piston to be reached in which the skirt is able to cause the device to pass from the injection configuration to the protection configuration, the inhibitor member remaining fitted to the head of the piston until occurrence of the first end-of-injection-stroke position.

11. A device according to claim 10, wherein, in the inhibit position, an inhibitor part of the inhibitor member extends into the head of the piston.

* * * * *